United States Patent [19]

Barrows

[11] Patent Number: 5,013,315

[45] Date of Patent: May 7, 1991

[54] SEMIABSORBABLE BONE PLATE SPACER

[75] Inventor: Thomas H. Barrows, St. Paul, Minn.

[73] Assignee: Minnesota Mining and Manufacturing Company, St. Paul, Minn.

[21] Appl. No.: 754,870

[22] Filed: Jan. 12, 1985

[51] Int. Cl.$^5$ ............................................. A61F 5/04
[52] U.S. Cl. .......................................... 606/71; 606/77
[58] Field of Search ..... 128/92 YO, 92 YP, 92 YPM, 128/92 YL, YQ, YG, YR, YF; 604/364, 368; 623/16; 606/71, 77

[56] References Cited

U.S. PATENT DOCUMENTS

| | | | |
|---|---|---|---|
| 3,463,158 | 8/1969 | Schmitt et al. | 128/92 YO |
| 3,952,334 | 4/1976 | Bokros et al. | 128/92 YO |
| 4,052,988 | 10/1977 | Doddi et al. | 128/92 YO |
| 4,279,249 | 7/1981 | Vert et al. | 128/92 |
| 4,297,993 | 11/1981 | Harle | 128/92 YP |
| 4,338,926 | 7/1982 | Kummer et al. | 128/92 |
| 4,512,038 | 4/1985 | Alexander et al. | 128/92 YO |
| 4,550,449 | 11/1985 | Tunc | 128/92 YO |

FOREIGN PATENT DOCUMENTS 2146535  4/1985  United Kingdom .

OTHER PUBLICATIONS

The Condensed Chemical Dictionary, 10th Edition Hawley, Copyright 1981.
*Webster's Ninth New Collegiate Dictionary*, Merriam, Webster Inc. Springfield, Mass. 1985 pp. 159 and 761.
J. Bone and Joint Surg. 64-B(1) 105 (1982).
The Developement of Fiber Reinforced Polymer Composites for Orthopedic Applications, Ph.D. Thesis, Univ. of Utah, 1976.
The Development of a Variable Stiffness, Absorbable Composite Bone Plate, Corcoran, et al., Chapter in Book Entitled "Current Concepts of Internal Fixation of Fractures", H. K. Uhthoff, Springer-Verlag (1980).
Pending U.S. Ser. No. 504,222, Filed Jun. 14, 1983.
Pending U.S. Ser. No. 404,105, Filed Aug. 2, 1982.

*Primary Examiner*—C. Fred Rosenbaum
*Attorney, Agent, or Firm*—Gary L. Griswold; Walter N. Kirn; Lorraine R. Sherman

[57] ABSTRACT

A medical prosthesis for use in bone fracture fixation comprises a bone plate, a bone plate spacer comprising a blend or mixture of a nonabsorbable polymer and a bioabsorbable polymer, and a means for fastening both the bone plate and the bone plate spacer to the bone.

20 Claims, 1 Drawing Sheet

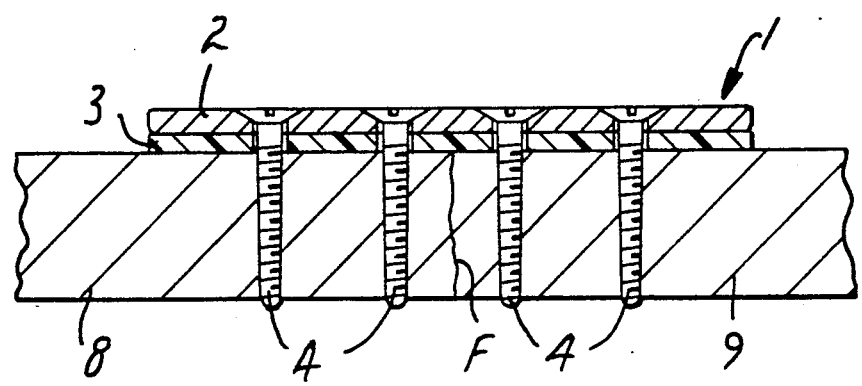

SEMIABSORBABLE BONE PLATE SPACER

FIELD OF THE INVENTION

The present invention relates to a prosthesis for use in bone fracture fixation. In another aspect, a method for bone fracture fixation using the prosthesis of the invention is disclosed.

BACKGROUND OF THE INVENTION

Broken bones, particularly severely broken bones, are often repaired using a technique known as internal fixation. The most commonly used fixation device is known as a bone plate or compression plate. This technique secures the bone fragments in place with fastening means such as screws placed through holes in the plate. The bone fragments may also be compressed together in an effort to facilitate bridging of the spaces between the bones.

Numerous different materials and designs have been used for the plates. It has been found that the initial and early strength of the plate is very important to immobilize the fragments during healing. Polymeric bone plates such as nonabsorbable polymer plates, e.g., K. Tayton et al., J. Bone and Joint Surg., 64-B(1), 105 (1982) and fiber reinforced nonabsorbable polymer composite plates, e.g., by G. B. McKenna, "The Development of Fiber Reinforced Polymer Composites for Orthopedic Applications," Ph.D. Thesis, University of Utah, 1976, have been described.

Absorbable polymer plates have also been described, e.g., by M. Virt, et al. in U.S. Pat. No. 4,279,249 and by Corcoran, et al., "The Development of a variable Stiffness, Absorbable Composite Bone Plate" in "Current Concepts of Internal Fixation of Fractures," H. K. Uhthoff, ed., Springer-Verlag, N.Y. (1980), where carbon fiber reinforced absorbable plates are described.

In most cases the material of choice for the bone plate remains a metallic alloy. Various steel alloys, generally varieties of stainless steel, are preferred. However, the use of steel plates for internal fixation has certain drawbacks. One of these is the phenomenon of stress-shielding, wherein stresses are exerted primarily on the plate rather the bone in the fracture region. This stress-shielding has been found to be the cause of significant bone resorption and consequent reduction of strength of the bone in the region of the healed fracture.

The use of polymeric bone plates has not satisfactorily solved the problem of stress-shielding, since the initial strength and rigidity of steel plates is desirable for most fractures. Attempts to solve the problem of stress shielding by providing polymeric washers or spacers in the bone fixation devices have recently been reported. Kummer and Coutts, U.S. Pat. No. 4,338,926 have described a bone fracture prosthesis wherein a bioabsorbable spacer or washer is used. These devices of the art are not successful in practice, presumably due to premature loss of structural integrity. They have been found to provide excessive callus formation, which indicates inadequate fixation and in some cases they permit catastrophic failure of the repair.

SUMMARY OF THE INVENTION

Briefly, the present invention provides a prosthesis for use in bone fracture fixation comprising a bone plate spacer comprising a blend or mixture of a bioabsorbable polymer with a nonabsorbable polymer.

The bioabsorbable/nonabsorbable polymer blend of the present invention provides a material for use as a bone plate spacer that gives nearly 100% (preferably at least 90%) normal bone porosity in the long term without plate removal, yet gives an early healing result equal to that achieved with a nonabsorbable polymer spacer (e.g. polyethylene). By proper selection of the polymers blended and the thickness of the spacer, it is possible to control the rate at which the mechanical properties of the spacer deteriorate to coincide with the rate of increase in bone strength due to healing and thereby avoid a catastrophic failure that may occur with a purely absorbable material. A further advantage of the partially-absorbable material is that the bone plate is protected from invasive bone growth that might otherwise engulf the plate upon spacer absorption. Protection from envelopment due to bone growth into the devices of the invention prevents the reestablishment of a stress protected environment at the fracture site. The prosthesis is essentially nonporous for several months, but porosity increases as the absorbable polymer is absorbed. Bone ingrowth does not occur due to the small pore size resulting from polymer absorption.

When a spacer is absorbed as in prior art inventions, the gap between the bone and the plate can permit excessive motion of the plate relative to the screws, a situation that promotes corrosion of the stainless steel. Because the bone plate spacer of the present invention retains its structural integrity due to the nonabsorbable polymer, this excessive motion does not occur.

The blends and mixtures of polymers of the invention are preferably selected to obtain low porosity and thus prevent bone ingrowth while the bioabsorbable component is being absorbed and when it has been absorbed. The porosity after bioabsorption of the absorbable component depends on the size of the domains of absorbable polymer in the original mixture or blend. The pores that result (after bioabsorption) should be 100 micrometers or less in average diameter, preferably 50 micrometers or less, to prevent bone ingrowth. In the present invention, in the range of 20 to 70 weight percent, preferably 40 to 60 weight percent, of the bone plate spacer is bioabsorbable. This property of the spacers allows eventual complete mechanical decoupling of the plate, the screw and the spacer from the bone due to chemical decoupling of the spacer material. The bone, the spacer, and bone plate are held together by fastening means such as screws, rivets or staples. To facilitate bone healing the composite prosthesis is mechanically joined by fastening means. During healing, the bioabsorbable component of the bone spacer allows for chemical decoupling of the bone plate and the spacer from the bone. The screws remain in the bone and prosthesis remains physically coupled (but chemically and mechanically decoupled) from the bone. This mechanical decoupling allows the bone to recover its strength during the later stage of healing known as bone remodelling.

The bone plate spacers of the invention are prepared from blends and mixtures of polymers which provide firm and resilient residual spacers after the bioabsorbable component has been absorbed.

Surprisingly, the devices of the invention combine the advantages of using bioabsorbable spacers (gradual decrease in stress shielding, prevention of osteoporosis, no need for a second operation for plate removal) with the advantages of using nonabsorbable spacers (avoid early catastrophic failure of device, prevent bone growth around the plate, avoid excessive motion of the plate relative to the fastening means) and avoid the disadvantages of the spacers of the art. The synergistic effect of the use of blends or mixtures of nonabsorbable and bioabsorbable spacers was unpredictable and surprising.

In another aspect, the present invention provides a method for bone fracture fixation comprising implanting a prosthesis comprising a partially-absorbable bone plate spacer comprising a nonabsorbable component and a bioabsorbable component to provide a resulting healed bone with near normal porosity with or without removal of the bone plate and the spacer. The bone plate spacer lies adjacent the bone, between the bone and the bone plate.

In this application:

"bioabsorbable" or "absorbable" means that the polymer is metabolized by the body and ultimately eliminated therefrom or used therein;

"bone plate" means a plate, preferably metallic, preferably with holes such as those currently in commercial use or to be used in the future to surgically repair fractured bones by securing the plate to the bone with fastening means, such as screws, rivets, or staples, placed through the holes;

"bone plate spacer" means a nonmetallic material placed between the bone plate and the bone;

"partially absorbable" or "semiabsorbable" means that a substantial portion (i.e., 10 to 100 weight percent) of the absorbable polymer component of a blend or mixture of absorbable and nonabsorbable components will become hydrolyzed, leached out, and removed from the blend or mixture in vivo one to three years post implantation;

"mixtures of nonabsorbable and bioabsorbable polymers" means that the two types of polymers are sufficiently mixed together and are sufficiently compatible or miscible that total removal of the bioabsorbable component can be achieved without physical disintegration of the nonabsorbable component;

"blend" means a very good mixture, not necessarily of sufficient homogeneity to provide thermal properties which are different from any of the components;

"chemical decoupling" means that sufficient chemical change (e.g., hydrolysis) has occurred in a material to permit complete relaxation of stress applied prior to chemical change (i.e., after chemical decoupling, stress applied to the material is no longer completely transmitted through the material);

"mechanical decoupling" means that several structural components fastened together and initially functioning as a composite no longer function as a composite (e.g., one of the structural component properties has undergone a change) although they remain tightly joined together; and "physical decoupling" means that in addition to mechanical decoupling, a measurable gap exists between structural components that were initially fastened securely together.

DESCRIPTION OF THE DRAWING

The Drawing shows a cross-sectional view of a medical prosthesis of the invention.

In one embodiment, as shown in the Drawing, the prosthesis 1 of the invention comprises steel bone plate 2 adjacent the surface of bone plate spacer 3 are fastened to both plate 2 and bone plate spacer 3 are fastened to both portions of a bone 8,9, having fracture site F, by means of screws 4.

DETAILED DESCRIPTION OF THE INVENTION

The present invention provides a medical prosthesis for use in bone plate fixation comprising a bone plate, a bone plate spacer comprising a blend or mixture of a nonabsorbable polymer and a bioabsorbable polymer affixed or adjacent to one surface of the bone plate, and a means for fastening both the bone plate and the bone plate spacer to the bone.

The bone plate spacer comprises bioabsorbable and nonabsorbable polymers present in the range of 20-70/-80-30 percent by weight, preferably 40-60/60-40 percent by weight. Preferably, the bone prosthesis according to the present invention enables healing to take place so that the bone achieves at least 90% normal bone porosity with or without plate removal after at least one year of healing. After total absorption of the bioabsorbable component, the voids present should have diameters of 100 micrometers or less, preferably 50 micrometers or less, most preferably 0.01 to 50 micrometers. The thickness of the spacer is used to control the rate of change in properties, and 1 to 2 mm thickness is desirable although thickness in the range of 0.5 to 5.0 mm can be useful. The shape of the spacer can vary, but generally it is the same as the bone plate, and it may be shaped to cover the sides of the bone plate as well.

The bone plate which generally is made of a strong, rigid material may be any standard bone plate material which provides adequate strength. It may be, and is preferably, a non-degradable metal plate, or it may be, for some purposes, a bioabsorbable plate which offers good strength for a sufficient time to allow the bone to regain its strength.

The means for fastening both the bone plate and the bone plate spacer to the bone may be any standard nonabsorbable or absorbable fastening means, e.g., screws, rivets, or staples. It is preferably a nonabsorbable fastening means. In the method and devices of the present invention a fastening means such as a screw could also be a mixture of nonabsorbable polymer and a bioabsorbable polymer with strength and durability at least equal to the strength and durability of the bone plate spacer.

The spacer comprises a combination, e.g. a mixture, not a copolymer, of a nondegradable polymer and a bioabsorbable polymer. The bioabsorbable polymer may be any physiologically-acceptable natural or synthetic bioabsorbable polymer such as those listed in TABLE I, below. Synthetic bioabsorbable polymers are preferred. Copolymers or mixtures of suitable bioabsorbable polymers are also included within the scope of suitable materials. That is, the bone plate spacer of the invention could consist of mixtures of two or more bioabsorbable polymers in addition to one or more nonabsorbable polymers. Natural polymers are preferably used in admixture with synthetic polymers.

TABLE I

A. Natural Polymers (1) Partially oxidized cellulose surgical hemostats (see U.S. Pat. No. 3,364,200) such as Oxycel ™ (fibrous surgical hemostatic material, Parke-Davis) and Surgicel ™ (woven fabric hemostatic material, Surgikos).

(2) Chitin and/or chitin derivatives (e.g. U.S. Pat. No. 4,074,366).

(3) Collagen, regenerated collagen or catgut suture material.

B. Synthetic Polymers (1) Polyamino acids, polyamino acid copolymers and derivatives such as partially esterified poly-L-glutamic acid (U.S. Pat. No. 3,371,069), amino acid-hydroxy acid copolymer (U.S. Pat. No. 3,773,737), and nylon 2/nylon 6 copolymer (W. J. Bailey, et. al., "Biodegradable Polyamides", *Proceedings of 3rd International Biodegradation Symposium,* Sharpley and Kaplan, eds., Applied Science Publishers Ltd., London, 1976, p. 765–773).

(2) Polyesters formed from diols and succinic and/or oxalic acid such as those described in U.S. Pat. Nos. 4,032,993 and 3,883,901, isomorphic copolyoxalates (U.S. Pat. No. 4,141,087), and poly(alkylene oxalates) (U.S. Pat. No. 4,140,678).

(3) Polymalic acid (U.S. Pat. No. 4,265,247).

(4) Polydioxanone (U.S. Pat. No. 4,052,988).

(5) Poly-beta-hydroxy acids such as polyhydroxybutyrate (U.S. Pat. No. 3,225,766).

(6) Poly-alpha-hydroxy acids such as polyglycolic acid, polylactic acid, copolymers of lactic and glycolic acids, and said polymers copolymerized with other polyesters (U.S. Pat. Nos. 4,118,470, 3,636,956, and 4,137,921).

(7) Polymers made from unsymmetrically-substituted 1,4-dioxane-2,5-diones (U.S. Pat. No. 3,960,152).

(8) Polyesteramides such as those described in U.S. Pat. Nos. 4,209,607 and 4,343,931.

(9) Copolymers of glycolide and trimethylene carbonate such as described in U.S. Pat. No. 4,429,080.

Preferred biodegradable polymers and copolymers for use in the invention are polylactic acid (U.S. Pat. No. 3,636,956), polyglycolic acid (U.S. Pat. No. 3,297,033), polydioxanone (U.S. Pat. No. 4,052,988), copolymers of glycolide and trimethylene carbonate, (U.S. Pat. No. 4,429,080) poly(lactide-co-glycolide) (U.S. Pat. No. 4,137,921) and poly(esteramides) such as poly(oxysuccinoyloxydodecane-1,12-di(amidocarbonylmethylene)-co-10 percent-oxysuccinoyloxy-4,9-dioxadodecane-1,12-di(amidocarbonylmethylene) and poly[oxysuccinoyloxyhexane-1,6-di(amidocarbonylmethylene)] (U.S. Pat. No. 4,343,931), and mixtures thereof. These polymers and copolymers are preferred because they are known to be well tolerated by the body upon implantation in addition to being absorbable. Mixtures of polymers allow for variation of properties of the spacers.

Nondegradable polymers and copolymers for use in the invention can be any of many nondegradable polymers such as polyalkylenes, e.g. polyethylenes, propylenes, polybutylenes and the like, nylons such as nylon 12, nylon 6, nylon 66 and the like, polyurethanes such as Lycra TM (Dupont), Estane TM (B.F. Goodrich), and the like. Preferably the nondegradable polymer is a polymer known to be acceptable as a permanent implant material such as Biomer TM (Ethicon), a special medical grade of Lycra as described in "Polyurethanes in Biomedical Engineering", Ed. H. Planck, G. Egbers and I. Syre, Elsevier, N.Y., 1984. Preferred nondegradable polymers are polyurethanes.

It is presently preferred to use mixtures of Lycra TM and poly[oxysuccinoyloxyhexane-1,6di(amidocarbonyl-methylene)] as the bone plate spacer of the invention.

The mixtures of polymers useful in the present invention are prepared by any suitable method which will provide an intimate or homogeneous mixture. Preferably the mixtures are prepared simply by dissolving the polymers in a suitable solvent, preferably an organic solvent such as dimethylformamide, trifluoroethanol or dimethylacetamide depending on the mixture of polymers selected, optionally heating at a temperature at which the polymer or polymers are stable, and then precipitating the polymer mixtures by cooling or pouring into a second solvent in which the first solvent is miscible but the polymers are insoluble. One of the polymers may be dissolved in a solvent, then the second polymer may be added to the solution and dissolved, or each polymer may be dissolved separately and the solutions then combined. The precipitation of the polymer mixture may be effected by cooling, e.g. rapid cooling, or by adding the polymer mixture solution to a liquid nonsolvent which causes precipitation.

The precipitated polymer mixtures may be separated from the liquid by any convenient method such as filtration, decantation or centrifugation.

The bone plate spacer is formed from the polymer blends or mixtures by any convenient method. For example, if the polymer mixtures are thermoplastic the bone spacers may be formed by melt pressing. If desired the polymer mixture can be deposited into molds and dried and shaped therein.

Alternatively, polymers can be blended together in a melt and formed into an article by coextrusion. The step of coextrusion can itself be a mixing step in the absence of solvent.

In the practice of the present invention, the method for bone fracture fixation comprises the steps of providing a bone plate spacer/bone plate prosthesis, and securing the prosthesis to the positioned bone by fastening means with the bone plate spacer portion of the prosthesis being adjacent the bone. In use, the spacer can be simply placed under the bone plate. Screw holes can be drilled through the spacer at the same time holes are drilled in the bone, or the spacer can be provided with pre-drilled holes. Alternatively the spacer can be attached to the bone plate to facilitate placement.

Objects and advantages of this invention are further illustrated by the following examples, but the particular materials and amounts thereof recited in these examples, as well as other conditions and details, should not be construed to unduly limit this invention.

EXAMPLE 1

A solution of polyurethane, 15.3% w/v in N,N-dimethylacetamide (Lycra TM, DuPont) was warmed to 100° C. Poly[oxysuccinoyloxyhexane-1,6-di(amidocarbonylmethylene)], hereinafter sometimes referred to as poly(ester-amide), was prepared by a method similar to that described in U.S. Pat. No. 4,343,931 and had an inherent viscosity of 1.33 (0.5% in 2,2,2-trifluoroethanol, measured at 30° C.). This polymer was dissolved in hot N,N-dimethylformamide, 10% w/v, and the solution was maintained at 100° C. Different amounts of the two solutions were mixed together to give new solutions containing:

(A) 60% poly(ester-amide): 40% Lycra (B) 40% poly(ester-amide): 60% Lycra (C) 20% poly(ester-amide): 80% Lycra The hot solutions were then separately poured into large volumes of rapidly stirred methanol, which resulted in precipitation of the blended polymers. The products were collected by filtration on Buchner funnels and dried under vacuum at 60° C. for several days.

The blends were formed into 1 mm thick slabs by melt pressing at 180° C. followed by cooling under slight pressure. The melt pressed samples were translucent, flexible, and strong with a perceivable increase in stiffness with increasing poly(ester-amide) content.

In order to estimate the properties of these samples after long term implantation in vivo, the samples were subjected to hydrolysis in refluxing 0.1N sodium hydroxide solution for 3 days to remove the poly(ester-amide) content. The samples were then soaked in distilled water and dried to give opaque white materials which had the same dimensions as the original samples but were strikingly softer, lighter, drapable and resilient. The decrease in weight resulting from this treatment indicated quantitative removal of the poly(ester-amide) content for samples A and B, but incomplete removal in sample C. Sample A was broken in half after freezing in liquid nitrogen and the fractured edge examined by scanning electron microscopy which revealed irregular shaped and interconnecting pores that were generally in the range of 5 to 50 micrometers in size.

The shear modulus of these samples before and after hydrolysis was measured using a dynamic mechanical analyzer (Polymer Laboratories, Inc., Stow, Ohio 44224). The results, listed in Table 1, show that hydrolysis resulted in a drop in modulus, providing a value almost 16 times lower than the original value for samples A and B. Sample C, as previously mentioned, was not completely devoid of poly(ester-amide), presumably because the high Lycra content inhibited removal of poly(ester-amide) under these conditions.

The modulus of the original samples before hydrolysis was proportional to the ratio of poly(ester-amide) to Lycra as shown in TABLE I. This indicated that the two polymers were thoroughly mixed together.

TABLE I

| | Shear Modulus of Poly(ester-amide)/Lycra Blends Before and After Hydrolysis in 0.1 N NaOH at 100° C. for 3 days | | |
|---|---|---|---|
| | Sample | Modulus (MPa) Before Hydrolysis | Modulus (MPa) After Hydrolysis |
| A | 60/40-Poly(ester-amide)/Lycra | 19.95 | 1.26 |
| B | 40/60-Poly(ester amide)/Lycra | 12.59 | 0.79 |
| C | 20/80-Poly(ester-amide)/Lycra | 5.01 | 1.99 |

In order to estimate the performance of these materials during the initial critical period of bone healing (approximately 3 months), an in vitro test was performed as follows. Samples A and B (10 mm×60 mm×1 mm) were placed in vials containing pH 7.4 phosphate buffered (0.05M) saline (0.9% sodium chloride) solution. As control materials, samples of the same dimensions were fabricated from the pure poly(ester-amide) and from poly(lactide—co 30%—glycolide) synthesized by a published procedure (D. K. Gilding and A. M. Reed, Biodegradable Polymers for Use in Surgery—Polyglycolic/Poly(lactic acid) Homo and Copolymers, Polymer, 20, 1459, 1979). The vials were placed in an incubator set at 37° C. Each week the samples were removed from the incubator, tested by gently flexing the polymer, placed in fresh buffer solution, and returned to the incubator. After only two weeks, the poly(lactide-co 30%-glycolide) sample broke upon gentle flexing. The poly(ester-amide) sample did not break until the sixth week, whereas samples A and B were unchanged during the full 3 month period. After 18 weeks, samples A and B formed creases upon flexing, but these creases did not develop into cracks or lead to sample breakage. Thus the polyurethane content provided structural integrity to the sample after the absorbable polymer component had lost significant mechanical strength.

EXAMPLE 2

Nylon-6 (Aldrich Chemical Co.) was dissolved in 2,2,2-trifluoroethanol to give a 10% w/v solution. Poly[oxysuccinoyloxyhexane-1,6-di(amidocarbonylmethylene)] [poly(ester-amide)] was also dissolved in 2,2,2-trifluoroethanol to give a 10% w/v solution. The two solutions were mixed together to give new solutions containing 20% poly(ester-amide)—80% nylon and 40% poly- (ester-amide)—60% nylon. These solutions were separately poured into large volumes of rapidly stirring ethyl acetate which resulted in precipitation of the blended polymers. As a control, some of the pure poly(ester-amide) solution was also precipitated in ethyl acetate. The polymer samples were collected by filtration onto Buchner funnels and dried under vacuum at 60° C. for several days. The polymers were then compression molded at 180° C. to give discs, 38 mm diameter×6 mm thick, which were translucent and amber colored.

Cylinders, 4 mm diameter×6 mm long, were cut from the discs and placed in 0.1N sodium hydroxide solution at room temperature. The solution was replaced every week with fresh solution and the test cylinders observed for changes in appearance.

The pure poly(ester-amide) cylinders gradually became smaller and by 3 weeks were completely dissolved. The nylon-poly(esteramide) blends, however, showed no change in dimension, but changed in color from amber to opaque white. One of the 40% poly(ester-amide) cylinders was cut in half with a sharp blade and the cut surface examined under the microscope. The core of the cylinder after 3 weeks in 0.N sodium hydroxide was still amber whereas the outer surface (approximately 25% of the radius) was opaque white, indicating loss of the poly(ester-amide) content.

It is known that this poly(ester-amide) requires at least six to nine months for compete absorption in vivo. (T. H. Barrows, S. J. Gibson, and J. D. Johnson, "Poly(ester-amides): In vivo Analysis of Degradation and Metabolism using Radiolabelled Polymer", Trans. Soc. Biomater, 7, 210, 1984). Thus the accelerated degradation of the poly(ester-amide) cylinders in 0.1N sodium hydroxide indicates that a 40% poly(ester-amide) nylon blend will require approximately six to nine months in vivo to lose poly(ester-amide) to a depth of 1 mm in the surface of articles molded from this blend. This reduction in the rate of poly(ester-amide) disappearance from the blend compared with the pure poly(ester-amide) demonstrated the utility of such a blend for the bone plate spacer application.

EXAMPLE 3

Estane TM 58309 polyurethane (B. F. Goodrich Company) was dissolved in N,N-dimethylformamide to give a 10% w/v solution. This solution was heated and mixed with different amounts of a 10% w/v solution of poly(oxysuccinoyloxyhexane-1,6-di(amidocarbonylmethylene)] [poly(ester-amide)] in hot N,N-dimethylformamide to give new solutions containing:

(D) 60% poly(ester-amide)—40% Estane
(E) 70% poly(ester-amide)—30% Estane (F) 80% poly(ester-amide)—20% Estane These solutions were separately poured into large volumes of methanol which resulted in precipitation of the blended polymers. The polymer samples were collected by filtration on Buchner funnels and dried under vacuum at 60° C. for several days. The polymers were then melt-pressed at 180° C. to give 0.15 mm thick films. The pale amber colored films were flexible, tough, and almost perfectly clear. The films were placed in 0.1N sodium hydroxide solution and held at 100° C. for 4 days. As a result, sample D became opaque white, soft, elastic, and drapable. Sample E had the same properties as D but could be easily torn, whereas sample F totally disintegrated under these conditions. Thus the poly(ester-amide)-polyurethane blend required a minimum polyurethane content of between 20% and 30% to maintain integrity after the poly(ester-amide) content was removed.

EXAMPLE 4

Using the procedure of Example 3, poly(lactide-co-30%-glycolide) as prepared in Example 1 can be used as the bioabsorbable component of a semiabsorbable bone plate spacer.

EXAMPLE 5

Using the procedure of Example 3, poly(glycolide)-co-trimethylene carbonate (Maxon TM suture material, American Cyanamid) can be used as the bioabsorbable component of a semiabsorbable bone plate spacer.

EXAMPLE 6

Using the procedure of Example 3, PDS TM (polydioxanone, Ethicon) can be used as the bioabsorbable component of a semiabsorbable bone plate spacer.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A medical prosthesis for use in bone fracture fixation comprising a bone plate, a bone plate spacer comprising a blend or mixture of a nonabsorbable polymer and a bioabsorbable polymer, and a means for fastening both said bone plate and said bone plate spacer to the bone.

2. The prosthesis according to claim 1 wherein said bone plate spacer comprises a polymeric blend or mixture having in the range of 20 to 70 percent by weight of at least one bioabsorbable polymer.

3. The prosthesis according to claim 2 wherein said spacer comprises a polymeric blend or mixture having in the range of 40 to 60 percent by weight bioabsorbable polymer.

4. The prosthesis according to claim 1 further comprising voids in said nonabsorbable polymer after absorption which have an average diameter of 100 micrometers or less.

5. The prosthesis according to claim 4 wherein said voids have an average diameter of 50 micrometers or less.

6. The prosthesis according to claim 1 wherein the bioabsorbable polymer of said bone plate spacer is selected from the group consisting of poly(ester-amides), poly(glycolic acid), poly(lactic acid), polydioxanone and poly(trimethylene carbonate) and copolymers and mixtures thereof.

7. The prosthesis according to claim 1 wherein the nonabsorbable polymer of said bone plate spacer is a polyurethane, a polyalkylene or a nylon.

8. The prosthesis according to claim 7 wherein said bioabsorbable polymer of said bone plate spacer is poly[oxysuccinoyloxyhexane-1,6-di(amidocarbonylmethylene)].

9. The prosthesis according to claim 1 wherein said fastening means is a screw.

10. A method for bone fracture fixation comprising the steps of:
   a. providing a medical prosthesis comprising a bone plate, a bone plate spacer comprising a blend or mixture of a nonabsorbable polymer and a bioabsorbable polymer, and a means for fastening bone said bone plate and said bone plate spacer to said bone with said bone plate spacer adjacent said bone, and
   b. securing said prosthesis to said bone by fastening means.

11. The method according to claim 10 wherein said fastening means is a screw, rivet, or staple.

12. The method according to claim 11 wherein said fastening means is a screw.

13. The method according to claim 10 wherein said bone plate spacer comprises a polymeric blend or mixture having in the range of 20 to 70 percent by weight of at least one bioabsorbable polymer.

14. The method according to claim 13 wherein said range is 40 to 60 weight percent.

15. The method according to claim 10 wherein after absorption said bioabsorbable polymer has voids having an average diameter of 100 micrometers or less.

16. The method according to claim 15 wherein said average diameter is 50 micrometers or less.

17. The method according to claim 10 wherein said bone prosthesis provides at least 90 percent of normal bone porosity with or without plate removal after at least one year of healing.

18. The method according to claim 10 wherein the bioabsorbable polymer of said bone plate spacer is poly(ester-amide), poly(glycolic acid), poly(lactic acid), polydioxanone, poly(trimethylene carbonate) and copolymers or mixtures thereof.

19. The method according to claim 10 wherein said nonabsorbable polymer of said bone plate spacer is a polyurethane, a polyalkylene, or a nylon.

20. The method according to claim 19 wherein said bioabsorbable polymer of said bone plate spacer is poly[oxysuccinoyloxyhexane-1,6-di(amidocarbonylmethylene)].

* * * * *

UNITED STATES PATENT AND TRADEMARK OFFICE
CERTIFICATE OF CORRECTION

PATENT NO. : 5,013,315

DATED : May 7, 1991

INVENTOR(S) : Thomas H. Barrows

It is certified that error appears in the above-identified patent and that said Letters Patent is hereby corrected as shown below:

Col. 1, line 34, "variable" should read -- Variable --.

Col. 1, line 45, "rather the bone" should read -- rather than the bone --.

Col. 8, line 46, "*vivo*" should read -- Vivo --.

Col. 8, line 57, "EXAMPLE" should be on the next line in front of "3".

Col. 9, claim 1, first line of the claim, delete ";".

Col. 9, claim 1, fourth line of the claim, after "polymer," insert -- said bone plate spacer having the function of maintaining its integrity after absorption of the bioabsorbable polymer so as to support the bone plate on the bone, --.

UNITED STATES PATENT AND TRADEMARK OFFICE
CERTIFICATE OF CORRECTION

PATENT NO.  : 5,013,315
DATED       : May 7, 1991
INVENTOR(S) : Thomas H. Barrows It is certified that error appears in the above-identified patent and that said Letters Patent is hereby corrected as shown below:

Col. 10, claim 10, sixth line of the claim, after "polymer" insert -- said bone plate spacer having the function of maintaining its integrity after absorption of the bioabsorbable polymer so as to support the bone plate on the bone, --.

Signed and Sealed this

Twenty-fourth Day of August, 1993

Attest:

BRUCE LEHMAN

*Attesting Officer*    Commissioner of Patents and Trademarks